(12) United States Patent  
Dietrich et al.

(10) Patent No.: US 8,345,236 B2  
(45) Date of Patent: Jan. 1, 2013

(54) METHOD AND APPARATUS FOR DETERMINING THE PARTICLES CONTAINED IN A PARTICLE STREAM

(75) Inventors: Stefan Dietrich, Chemnitz (DE); Guenter Eckardt, Chemnitz (DE); Michael Koehler, Oberlungwitz (DE)

(73) Assignee: Parsum GmbH, Chemnitz (DE)

( * ) Notice: Subject to any disclaimer, the term of this patent is extended or adjusted under 35 U.S.C. 154(b) by 728 days.

(21) Appl. No.: 12/299,744

(22) PCT Filed: Apr. 30, 2007

(86) PCT No.: PCT/DE2007/000795  
§ 371 (c)(1),  
(2), (4) Date: May 20, 2009

(87) PCT Pub. No.: WO2007/128279  
PCT Pub. Date: Nov. 15, 2007

(65) Prior Publication Data  
US 2009/0219529 A1    Sep. 3, 2009

(30) Foreign Application Priority Data  
May 5, 2006    (DE) .................. 10 2006 021 487

(51) Int. Cl.  
*G01N 15/02* (2006.01)  
(52) U.S. Cl. ................................. 356/335  
(58) Field of Classification Search .................. None  
See application file for complete search history.

(56) References Cited

U.S. PATENT DOCUMENTS

| | | | |
|---|---|---|---|
| 3,737,633 A * | 6/1973 | Collineau | 377/50 |
| 3,864,551 A * | 2/1975 | Oefinger | 377/12 |
| 3,867,613 A * | 2/1975 | Schoon | 377/10 |
| 3,936,739 A * | 2/1976 | Hogg | 377/50 |
| 4,009,443 A * | 2/1977 | Coulter et al. | 327/26 |
| 4,021,117 A * | 5/1977 | Gohde et al. | 356/39 |
| 4,110,604 A * | 8/1978 | Haynes et al. | 377/10 |
| 4,447,883 A * | 5/1984 | Farrell et al. | 702/26 |
| 4,510,438 A * | 4/1985 | Auer | 324/71.4 |
| 4,981,580 A * | 1/1991 | Auer | 209/3.1 |
| 4,984,889 A * | 1/1991 | Sommer | 356/336 |
| 5,204,884 A | 4/1993 | Leary et al. | |
| 5,296,910 A * | 3/1994 | Cole | 356/28.5 |
| 5,452,237 A | 9/1995 | Jones, Jr. | |
| 5,561,516 A | 10/1996 | Hairston et al. | |
| 6,118,531 A | 9/2000 | Hertel et al. | |
| 6,794,671 B2 * | 9/2004 | Nicoli et al. | 250/574 |

FOREIGN PATENT DOCUMENTS

| | | |
|---|---|---|
| DE | 197 18 875 C1 | 10/1998 |
| DE | 198 22 652 A1 | 11/1999 |
| DE | 199 11 654 C1 | 12/2000 |
| EP | 0 924 510 A1 | 6/1999 |
| EP | 1 039 289 A2 | 9/2000 |
| GB | 1 588 170 | 4/1981 |

* cited by examiner

*Primary Examiner* — Gordon Stock, Jr.

(74) *Attorney, Agent, or Firm* — Crowell & Moring LLP

(57) ABSTRACT

A method and an apparatus for determining the particle content of a particle stream using a source of light and two receivers arranged offset from one another in the flow direction of the particle stream. The receivers provide an electrical signal to an evaluation unit as a function of the radiation intensity which they receive, and this signal makes possible a determination of the flow velocity and particle size. Coincident passage of two particles is indicated by a pulse occurring in the signal due to a "roof collapse" in the pulse caused by a weakening of the radiation intensity as the particles pass a receiver.

20 Claims, 3 Drawing Sheets

Figure 1:
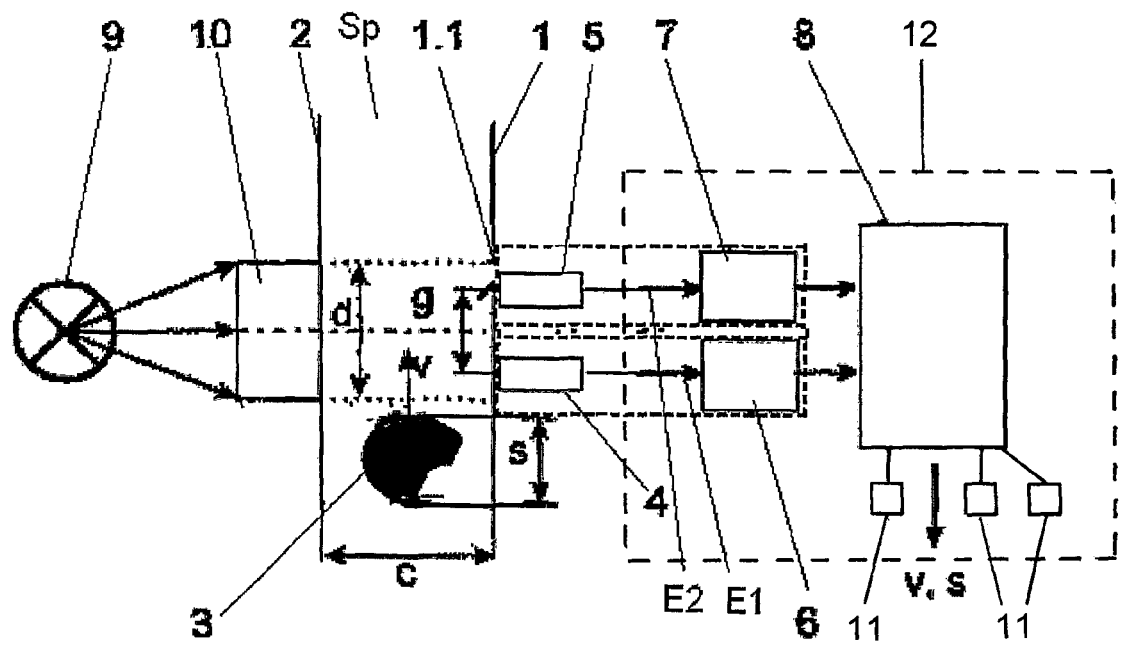

METHOD AND APPARATUS FOR DETERMINING THE PARTICLES CONTAINED IN A PARTICLE STREAM

The invention relates to a method and apparatus for determining the particles contained in a particle stream in accordance with the generic term of the first patent claim.

A device for determining the velocity and the size of particles has been known from DE 199 11 654 C1, wherein the particles are illuminated in a measuring volume with primary light from a lighting device, wherein the light influenced by the particles is imaged onto two light receivers which are arranged side by side in the direction of motion, and wherein the size of the particles is determined from time measurements, and the circular light receiving area of the first light receiver is surrounded by the annular light receiving area of the second light receiver. In DE 197 18 875 C1, a method for determining the particles contained in a gaseous or liquid carrier medium is described, by which very small particle sizes can be determined, and statements with regard to the geometric shape can be made. This is achieved by operating at least three light sources aimed at a measuring volume and at least three detectors at the same time, and evaluating in a correlated manner the scattered light values determined by the detectors. The disadvantage of the aforementioned solutions is that coincidence detection is not possible, so that two or more particles immediately succeeding each other are not identified as individual particles, but as one single larger particle. An optical particle counting system with coincidence detection is known from DE 198 22 652 A1. By examining pulse height, pulse length, and simultaneous sensing of the flow velocity, the voltage pulse generated by one or more particles is examined for possible coincidences. Coincidence errors are evaluated, and pulse height and pulse length can be stored in the form of a calibration table or characteristic curve in dependence on the particle diameter. In addition, a constant flow velocity must be used, or the flow velocity must also be recorded.

Publication U.S. Pat. No. 5,561,515 A describes an apparatus for determining (size and velocity) of particles contained in a particle stream by which apparatus two beam paths 32a, 32b are generated which are arranged offset to one another in flow direction and which generate a radiation intensity profile in the measuring volume which profile has a "roof collapse" in the direction of flow. An electrical signal is supplied to an evaluation unit in dependence on the received radiation intensity, and the coincidence is determined by comparing the shape of the curve of the signal with the "roof collapse".

An apparatus for determining the particles contained in a particle stream has been known from U.S. Pat. No. 5,793,478 A with a source of radiation generating a beam which has an intensity profile along the particle path with at least one "roof collapse", wherein the signal provided by a receiver is generated in dependence on the path of the particle(s), and a coincidence of two particles can be determined by comparison with the intensity profile during the passage through the beam or incomplete passage of particles through the beam. The three aforementioned systems are relatively complex.

It is the main object of the invention to develop an apparatus for determining the particles contained in a particle stream permitting a simple detection and correction of coincidences, if required, which can also be used for particle streams with an unknown very broad velocity distribution and broadly distributed particle sizes.

This main object is solved by the characteristic features of the first patent claim. Beneficial designs can be gathered from the sub-claims.

The method for determining the particles contained in a particle stream is carried out using a source of radiation and two receivers arranged offset to one another in flow direction, which receivers provide an electrical signal to an evaluation unit in dependence on the radiation intensity received during the passage of the particle stream, wherein the electrical signal (in addition to determining the flow velocity and particle size) serves to detect coincidences, and a pulse occurring in the signal due to a weakening of the radiation intensity while the particles are passing a receiver indicates a coincidence by a "roof collapse" in the pulse.

In this process, the receiver(s) are not completely shaded during the entire period of passing of the particles, whereby a radiation arrives in the respective receiver for a short time during the passage of the particles, so that the "roof collapse" occurs in the case of a coincidence.

It is possible to form a size distribution of detected coincidences and to deduct this distribution as correcting distribution from the measured particle size distribution. Furthermore, a distribution of non-detectable coincidences can be inferred from the distribution of detected coincidences, wherein the distribution of non-detectable coincidences can also be deducted as correcting distribution from the measured particle size distribution.

Alternatively, detected coincidences can be rejected as invalid measurements. The assignment of the signals is effected by carrying out a cross correlation between the first signal of a first receiver and the second signal of a second receiver in order to determine an average time lag between the two signals. Starting from a pulse with a position X in the first signal of the first receiver, a pulse is searched at the position X+t (and at increasing distances around this position) in the second signal of the second receiver. By examining predetermined tolerances for the pulse width, it can now be determined whether a pulse produced in the second signal is identical with the pulse produced in the first signal. This is of particular significance if there are very big differences between the velocities, thereby giving rise to the risk of faulty measurements.

In order to identify the degree of contamination, the zero level between the individual pulses is recorded in the first signal of the first sensor and/or the in the second signal of the second sensor. This zero level is evaluated as the measure for a contamination of a transparent wall surrounding the measuring gap. An upward shift of the zero level indicates a stronger contamination.

Furthermore, it is possible to indicate the condition during operation by means of one or more indicating unit(s) which is/are arranged together with the first sensor, the second sensor, and the evaluating unit in a common housing of the measuring probe.

Preferably,
the On/Off condition is indicated by means of a first indicating unit,
the laser intensity is indicated by means of a second indicating unit, and
the signal strength is indicated by means of a third indicating unit.

The apparatus for determining the particles contained in a particle stream has a radiation source and two receivers arranged offset to one another in flow direction which receivers provide an electrical signal to an evaluation unit in dependency on the radiation intensity received during the passage of the particle stream, wherein a coincidence is determined from a pulse occurring in the curve shape of the signal during the passage of the particles and a "roof collapse" present in the pulse.

Furthermore, a cross correlation is carried out in the evaluation unit between the first signal of the first receiver and the second signal of the second receiver for determining an average time lag between the two signals.

With a pulse at a position X in the first signal of the first receiver, a pulse at the position X+t is determined in the second signal of the second receiver, whereby tolerances for the pulse width predetermined in the evaluation unit can be evaluated.

The apparatus further has a measuring gap with a transparent wall behind which wall the first sensor and the second sensor are arranged, wherein the zero level between the individual pulses can be evaluated in the evaluation unit as the measure for a contamination of the wall.

Advantageously, one or more indicating unit(s) is/are arranged in a common housing together with the first sensor, the second sensor and the evaluation unit. A first indicating unit shows the condition On/Off, a second indicating unit shows the laser intensity of the radiation source (light source), and a third indicating unit shows the signal strength. The indicating unit(s) is/are preferably formed as LED/LEDs, having different colors corresponding to the condition to be indicated.

With the solution according to the invention, it is easily possible, in addition to the known measurement of the flow velocity and the particle size, to carry out a coincidence detection and correction and a contamination detection, and to signal different conditions and possible errors of the measuring probe.

In the following, the invention is explained in more detail on the basis of exemplary embodiments and associated drawings. In these drawings, FIG. 1: is a schematic diagram of the apparatus, FIG. 2: is the signal curve when a particle is detected, FIG. 3: is a simplified representation of the apparatus with two particles positioned side by side, FIG. 4: is the signal curve when two particles are detected, FIG. 5: is the curve shape of measured particle size distribution, correction distribution of the measured and not measured coincidences, and result distribution, FIG. 6: is a diagram of the occurring pulses at low particle concentration with normal assignment of the signals, FIG. 7: is a diagram of the occurring pulses at high particle concentration with faulty assignment of the signals, FIG. 8: is a diagram of the pulse signals with uncontaminated and contaminated wall of the measuring gap.

FIG. 1 shows a schematic diagram of the apparatus used for measuring the particles 3 present in a flow. In this case, a water flow is moving through a measuring gap Sp with a width c, wherein the gap is formed by a translucent wall 1, 2. Particles 3 of a size s present in the water flow are moved together with the current of the water in flow direction at a velocity v. On one side, a first receiver E1 (formed by optical wave guide 4 and opto-electronic transducer 6) and a second receiver E2 (formed by optical wave guide 5 and opto-electronic transducer 7) are arranged in tandem in the direction of the flow. The first and the second receiver E1, E2 are connected with an evaluation unit 8. On the opposite side of the measuring gap Sp, a radiation source 9 is provided (preferably a light source in the form of a laser), which a collimation lens system 10 is assigned to, by which a parallel light bundle with diameter d is generated. The diameter d of the light bundle and the width c of the measuring gap Sp define the measuring volume adjoining the optical effective area 1.1 of the translucent wall 1 on the side of the receivers E1, E2. A plurality of indicator units comprising light emitting diodes 11 are arranged in a common housing 12 together with a sensor of the first receiver E1, a sensor of the second receiver E2 and the evaluation unit 8.

Figure 2:
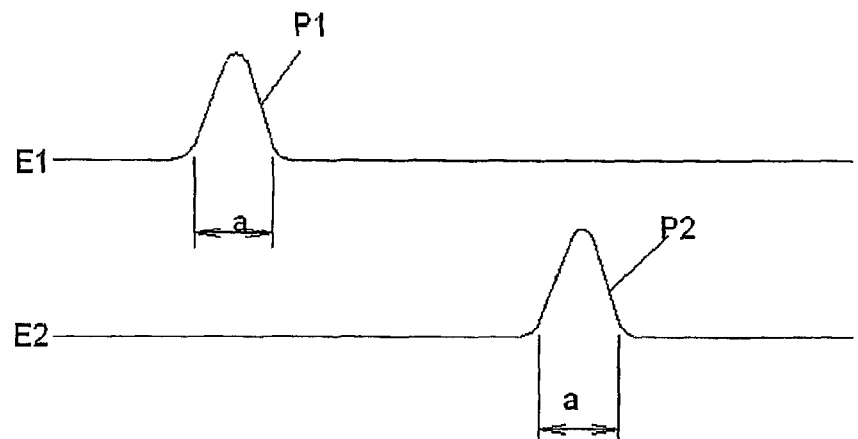

When a particle 3 moves through the measuring gap Sp in the water current at a velocity v, this particle, due to the light source 9, produces a shadow on the opposite side on the optical effective area 1.1 in the area of receiver E1, and after a time difference To, a shadow in the area of receiver E2. By the first receiver E1, a first pulse P1, and by the receiver E2, a second pulse P2 are sent as a signal to the evaluation unit. In the latter, the velocity v and the particle size s are calculated and indicated as well as stored, if required, as is known and described in DE 199 11 654 C1. The signal curve during detection of a particle is shown in FIG. 2.

Figure 3:
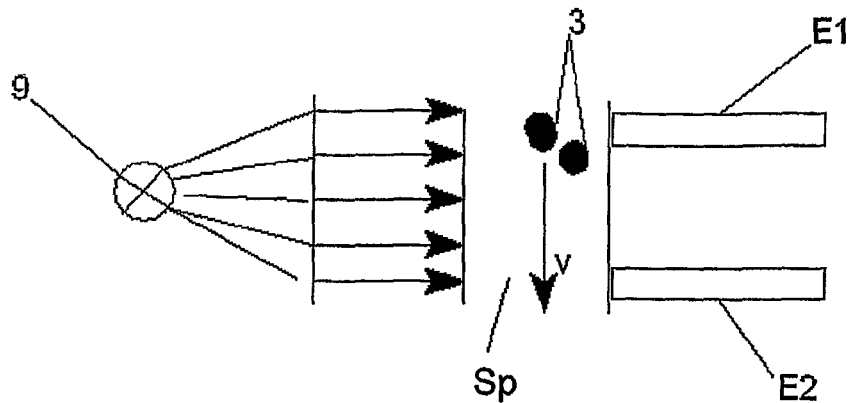

The simplified representation of the apparatus with two particles 3 positioned side by side is shown in FIG. 3. The problem here is, that two or more particles immediately succeeding each other are not clearly spaced, which is why they are not measured as several separate particles, but as one single larger particle 3.

Figure 4:
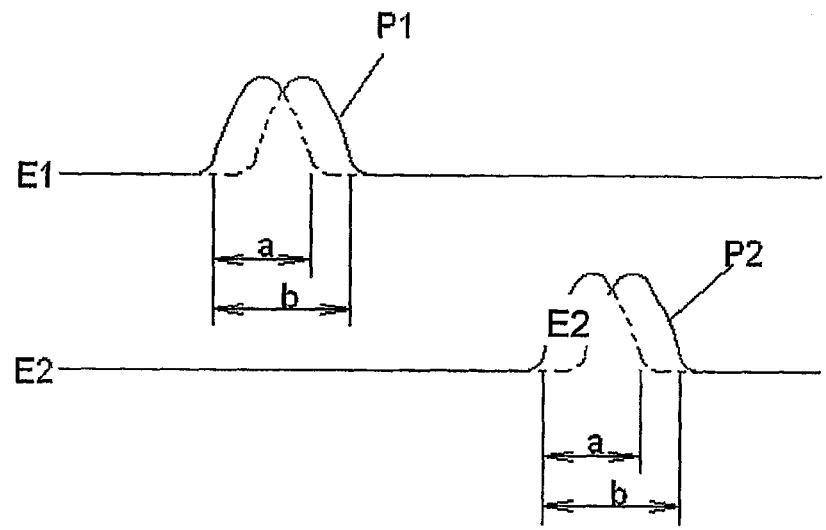

FIG. 4 shows the signal curve during detection of the two particles 3. It can be seen that in the signal curve of the first receiver E1 and of the second receiver E2 in pulse P1 and P2 in the plateau region of the pulses P1 and P2, a "roof collapse" occurs, which is the result of the fact that the receiver is not completely shaded during the entire period of the passing of the two particles, since the area of the shadow is reduced for a short time during the passage of the particles, and then increased again. Due to this "roof collapse", a coincidence can be detected and evaluated, which may either be rejected as an invalid measuring result, or used for correction of the measurement. In FIG. 4, measure a represents the actual size of the particle, and measure b the apparent and incorrect size.

Figure 5:
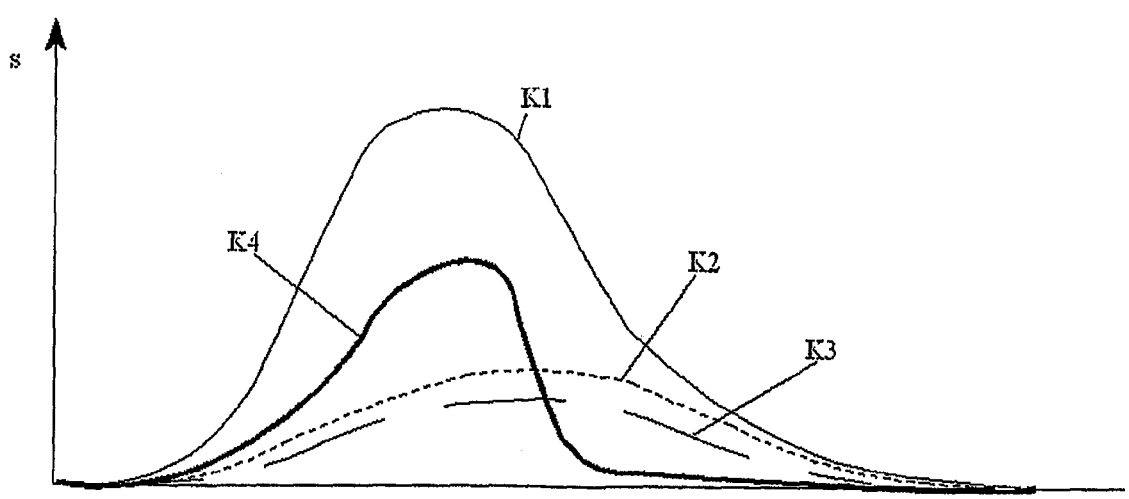

Pursuant to FIG. 5, the detected coincidence can also be used to correct the measurements carried out. For this purpose, curve K1 is the measured particle size distribution, curve K2 is the correction distribution of the measured coincidence, curve K3 is the correction distribution of the non-detectable coincidence, and curve K4 is the result distribution.

Figure 6:
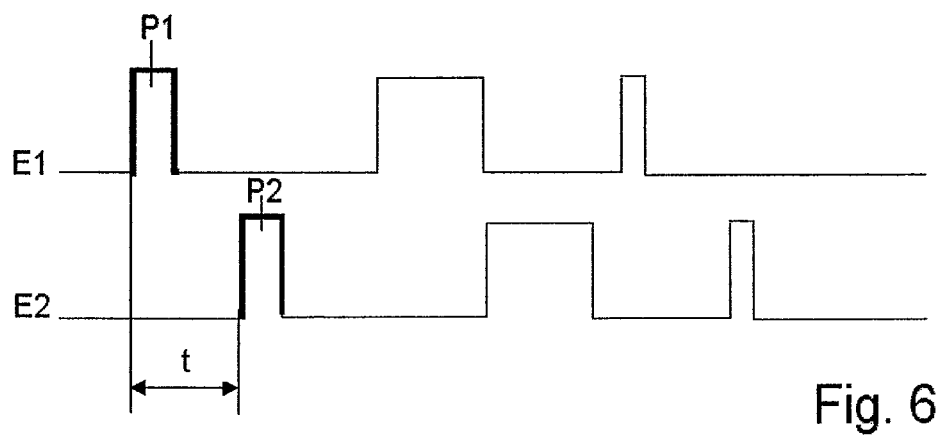
Figure 7:
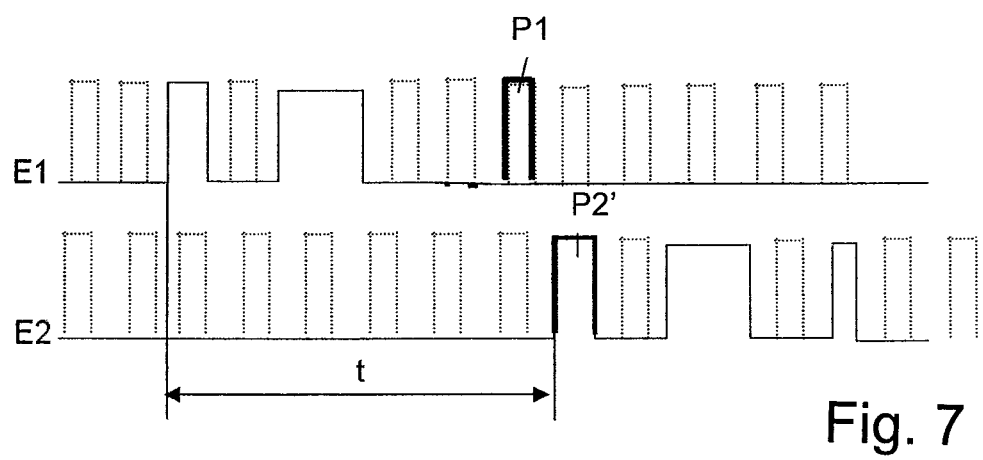

The assignment of the signals results from the diagrams according to FIGS. 6 and 7, wherein FIG. 6 shows the diagram of the occurring pulses at low particle concentration with normal assignment of the signals, and FIG. 7 shows the diagram of the occurring pulses at high particle concentration with a faulty assignment of the signals.

According to FIG. 6, at low particle concentration levels, pulse P1 of the second receiver E2 follows immediately within a short time t upon pulse P1 of the first receiver E1.

According to FIG. 7, pulse P1 recorded in receiver E1 was incorrectly assigned to pulse P2' recorded in receiver E2.

If, according to FIG. 6, a relatively long time t is required between the pulses P1 and P2, this is an indication of an incorrect assignment.

The correct assignment of the particles is realised via the pulse width, wherein it is started from the assumption that the same pulse width is produced by one particle in both signal curves.

With the solution according to the invention, it is also possible to determine the degree of contamination of the transparent walls 1, 2 of the measuring gap, in order to be able to make statements with regard to a required cleaning.

Previously, it was common to evaluate the amplitude and to compare it to the original condition; however, this does not result in a secure determination of the degree of contamination.

Figure 8:
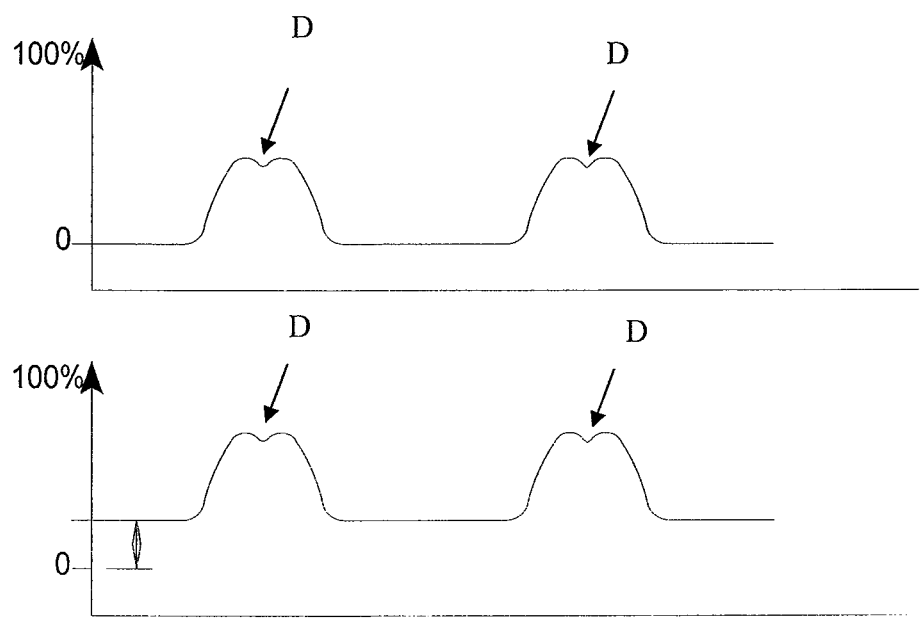

Therefore, for the first time, the zero level between the individual pulse signals output in the first and/or second receiver is evaluated as a measure for contamination. FIG. 8 shows the diagram of the pulse signals with uncontaminated and contaminated wall of the measuring gap. The upper diagram shows the pulse signals with uncontaminated wall, and the lower diagram shows the pulse signals with a contaminated wall. This makes it clear that the zero level increases with contamination (lower diagram). Further, "roof collapse" D can be seen, which results from the decrease and re-increase of the pulse signals. It is possible to signal the required cleaning at a predetermined zero level.

For this purpose, appropriate LEDs may be provided in the housing of the measuring probe (not shown), indicating the corresponding condition. Furthermore, power on/off (e.g. green for "on"), the laser intensity (e.g. green for "sufficient", red for "too weak") can be indicated by appropriate LEDs.

The solution according to the invention ensures reliable particle measurement which, in addition to the determination of flow velocity and particle size by detection and assessment of coincidences, guarantees a high measuring accuracy. In particular, a correct measurement of the particle size is ensured. Due to the novel assignment of the measuring values, the indication of the degree of contamination and of the operating condition of the measuring probe, incorrect measurements and operating errors are avoided.

LIST OF REFERENCE NUMERALS

1 Wall
1.1 Optical effective area
2 Wall
3 Particle
4 Optical wave guide
5 Optical wave guide
6 Opto-electronic transducer
7 Opto-electronic transducer
8 Evaluation unit
9 Light source
10 Collimation lens system
a actual size of the particle
b apparent, incorrect size of the particle
D "Roof Collapse"
E1 First receiver
E2 Second receiver
K1 Curve of the measured particle size distribution
K2 Curve of the correction distribution of the measured coincidence
K3 Curve of the correction distribution of the non-detectable coincidence
K4 Curve of the result distribution
P1 Pulse 1
P2 Pulse 2
To Time difference
s Particle size
Sp Gap
t Time
v Velocity

The invention claimed is:

1. A method for determining particles contained in a particle stream, using a source of radiation and two receivers arranged offset to one another in a flow direction of the stream for receiving radiation from said radiation source, wherein each receiver provides an electrical signal to an evaluation unit as a function of the intensity of radiation received;
the flow velocity and a measured particle size distribution of particles in the stream are determined from said signals;
a roof collapse occurring in a pulse in a signal caused by a weakening of the radiation intensity when two particles pass a receiver indicates a coincident passage of two particles, and
a size distribution of detected coincident passages is formed and deducted as a correction distribution from the measured particle size distribution.

2. A method according to claim 1, wherein the receivers are not completely shaded during passage of particles, whereby the roof collapse is caused to occur in case of coincident passage of two particles.

3. A method according to claim 1, wherein a zero level between individual pulses in a signal of at least one of said first and second receivers is recorded and evaluated as a measure of contamination of a transparent wall surrounding a measuring gap.

4. A method according to claim 1, wherein at least one indicator unit is provided for indicating a condition of a measuring probe during operation, said at least one indicator unit being arranged together with a sensor of the first receiver, a sensor of the second receiver, and the evaluation unit in a common housing.

5. A method according to claim 1, wherein a distribution of non-detectable coincidences can be concluded from the size distribution of detected coincident passages.

6. A method according to claim 1, wherein detected coincidences are rejected as invalid measurements.

7. A method according to claim 5, wherein the distribution of non-detectable coincidences is deducted as correction distribution from the measured particle size distribution.

8. A method according to claim 6, wherein in dependence on a pulse at a position X in a signal of the first receiver, a pulse is searched at position X+t in a signal of the second receiver.

9. A method according to claim 6, wherein predetermined tolerances for pulse width are examined to determine whether a pulse produced in a signal of the second receiver is identical with a pulse produced in a signal of the first receiver.

10. An apparatus for determining particles contained in a flowing particle stream, said apparatus comprising a source of radiation and two receivers arranged offset to one another in a flow direction of the particle stream, said receivers receiving radiation from said radiation source and each receiver providing an electrical signal to an evaluation unit as a function of the received radiation intensity, and said evaluation unit evaluating the electrical signals to determine the flow velocity and a measured particle size distribution of the particles in the stream; wherein a roof collapse occurring in a pulse in a signal caused by a weakening of the received radiation intensity when more than one particle passes a receiver indicates a coincident passage of more than one particle, and
the evaluation unit generates a size distribution of detected coincidences as a corrective distribution and subtracts this corrective distribution from the measured particle size distribution to obtain a corrected particle size distribution.

11. An apparatus according to claim 10, wherein a cross-correlation is carried out in the evaluation unit from a signal of the first receiver and a signal of a second receiver for determining an average time lag between the two signals, which time lag is caused by a particle.

12. An apparatus according to claim 10, wherein in the case of a pulse produced by a particle at a position X in a signal of the first receiver, a pulse in a signal of the second receiver is determined at position X+t.

13. An apparatus according to claim 10, wherein predetermined tolerances for a pulse width are evaluated in the evaluation unit.

14. An apparatus according to claim 10, wherein:
said apparatus comprises a measuring gap having a transparent wall;
sensors of the first and second receivers are arranged behind said transparent wall, and
a zero level between individual pulses produced by particles passing through said measuring gap past said sensors can be evaluated in the evaluation unit as a measure of contamination of the transparent wall of the measuring gap.

15. An apparatus according to claim 10, wherein at least one indicator unit is arranged in a common housing together with a sensor of the first receiver, a sensor of the second receiver, and the evaluation unit.

16. An apparatus according to claim 15, wherein said at least one indicator unit comprises an indicator unit for indicating whether a sensor is in an on condition or in an off condition.

17. An apparatus according to claim 15, wherein said indicator units comprise light emitting diodes.

18. An apparatus according to claim 16, wherein said source of radiation comprises a laser, and said apparatus comprises an indicator unit for indicating the intensity of radiation emitted from said laser.

19. An apparatus according to claim 18, wherein said apparatus comprises an indicator unit for indicating signal strength.

20. An apparatus according to claim 17, wherein the light emitting diodes emit different colors of light to indicate different conditions.

* * * * *